United States Patent
Henning et al.

(10) Patent No.: US 11,130,983 B2
(45) Date of Patent: Sep. 28, 2021

(54) SAMPLE PREPARATION CARTRIDGES AND METHODS FOR USING SAME

(71) Applicant: Abbott Molecular Inc., Des Plaines, IL (US)

(72) Inventors: Timothy P. Henning, Vernon Hills, IL (US); Joseph P. Skinner, Abbott Park, IL (US); Jody L. Keck, Abbott Park, IL (US); Chadwick M. Dunn, Abbott Park, IL (US); Wesley W. Addison, II, Chicago, IL (US); Timothy J. Patno, Abbott Park, IL (US); Sonal Sadaria Nana, Chicago, IL (US); Mark Talmer, Pepperell, MA (US); Austin Lines, Lebanon, NH (US); Daniel J. Harris, Deerfield, NH (US); Eric D. Yeaton, Epsom, NH (US)

(73) Assignee: Abbott Molecular Inc., Des Plaines, IL (US)

(*) Notice: Subject to any disclaimer, the term of this patent is extended or adjusted under 35 U.S.C. 154(b) by 242 days.

(21) Appl. No.: 15/460,186

(22) Filed: Mar. 15, 2017

(65) Prior Publication Data
US 2017/0268038 A1  Sep. 21, 2017

Related U.S. Application Data

(60) Provisional application No. 62/308,618, filed on Mar. 15, 2016.

(51) Int. Cl.
| | |
|---|---|
| *B01L 3/00* | (2006.01) |
| *C12Q 1/6806* | (2018.01) |
| *B01L 7/00* | (2006.01) |
| *C12N 15/10* | (2006.01) |

(52) U.S. Cl.
CPC ........ *C12Q 1/6806* (2013.01); *B01L 3/50851* (2013.01); *B01L 3/50853* (2013.01);
(Continued)

(58) Field of Classification Search
CPC .............. B01L 3/5085; B01L 2300/0829
(Continued)

(56) References Cited

U.S. PATENT DOCUMENTS

| | | |
|---|---|---|
| 5,035,861 A | 7/1991 | Grandone |
| 5,605,665 A | 2/1997 | Clark et al. |

(Continued)

FOREIGN PATENT DOCUMENTS

| | | |
|---|---|---|
| EP | 1767623 | 3/2007 |
| WO | 2015/154622 | 10/2015 |

(Continued)

OTHER PUBLICATIONS

Fang et al. (2007) "Automation of Nucleic Acid Isolation on KingFisher Magnetic Particle Processors" JALA 12(4): 195-201.

*Primary Examiner* — Natalia Levkovich
(74) *Attorney, Agent, or Firm* — Edward J. Baba; Mandar A. Joshi; Bozicevic, Field & Francis LLP

(57) ABSTRACT

Aspects of the present disclosure include sample preparation cartridges including a frame that includes a plurality of wells integrated therewith, where the plurality of wells have a closed bottom and an open top. The frame further includes an opening within the frame having a reaction vessel (RV) or RV cap removably disposed therein, where the plurality of wells and the opening are linearly arranged relative to each other. Also provided are sample preparation cartridges that include a frame, two or more cartridge separation projections on a top side of the frame, and two or more cartridge separation projections on a bottom side of the frame. The cartridge separation projections separate the cartridge and a different cartridge when the cartridge and different cartridge are stacked. Methods of using the sample preparation cartridges, as well as nucleic acid sample preparation units that include the sample preparation cartridges, are also provided.

30 Claims, 8 Drawing Sheets

(52) U.S. Cl.
CPC ................ B01L 7/52 (2013.01); B01L 7/525 (2013.01); C12N 15/1013 (2013.01); B01L 2200/10 (2013.01); B01L 2300/042 (2013.01); B01L 2300/0829 (2013.01); B01L 2300/0848 (2013.01); B01L 2300/0861 (2013.01); B01L 2400/0478 (2013.01)

(58) Field of Classification Search
USPC ................................. 422/552, 553, 551, 562
See application file for complete search history.

(56) References Cited

U.S. PATENT DOCUMENTS

| | | | |
|---|---|---|---|
| 2002/0006361 A1* | 1/2002 | Sanadi | ................ B01L 3/5025 422/400 |
| 2002/0068022 A1 | 6/2002 | Schneider | |
| 2008/0165665 A1 | 7/2008 | Martin et al. | |
| 2009/0136386 A1* | 5/2009 | Duffy | ................ F16K 99/0061 422/400 |
| 2013/0020202 A1 | 1/2013 | Feiglin et al. | |
| 2013/0130369 A1 | 5/2013 | Wilson et al. | |
| 2013/0288358 A1 | 10/2013 | Handique | |
| 2014/0322103 A1 | 10/2014 | Mcdevitt et al. | |
| 2015/0298120 A1 | 10/2015 | Westberg et al. | |

FOREIGN PATENT DOCUMENTS

| | | |
|---|---|---|
| WO | 2017/160980 | 9/2017 |
| WO | 2017/161053 | 9/2017 |
| WO | 2017/161058 | 9/2017 |

* cited by examiner

A

B

SAMPLE PREPARATION CARTRIDGES AND METHODS FOR USING SAME

CROSS-REFERENCE TO RELATED APPLICATIONS

This application claims the benefit of U.S. Provisional Patent Application No. 62/308,618 filed Mar. 15, 2016, which application is incorporated herein by reference in its entirety.

INTRODUCTION

Nucleic acid isolation and purification is a set of molecular biology techniques used for the extraction of DNA and RNA for use in downstream applications. Nucleic acid isolation and purification approaches include column-based isolation and purification, reagent-based isolation and purification, magnetic bead-based isolation and purification, and other technologies. Reagents, kits and instruments that find use in isolating and purifying nucleic acids are available. Poor sample preparation can lead to suboptimal results in downstream applications, and it is for this reason that optimized versions of kits have emerged to address variation in sample source, be it blood, plant tissue, fungi, or bacteria.

A system that automates steps to perform nucleic acid amplification assays from sample processing through amplification, detection, and data reduction is the Abbott m2000 System. This system includes the Abbott m2000 sp module which reads and processes bar coded primary sample tubes and processes up to 96 specimens, controls, and calibrators in batch mode. The sample preparation process consists of releasing the nucleic acid target from its native biological source (e.g., lysis of cells, such as patient cells or microorganisms) using chaotropic nucleic acid extraction technology, binding of nucleic acids to a solid phase (magnetic particles) using silica or iron oxide nucleic acid chemistry, separation of the solid phase from the residual lysis solution using magnetic separation technology, washing to remove unwanted materials, and elution or separation of nucleic acid from the solid phase using fluid handling technology. At the completion of the automated sample preparation protocol, the operator seals and manually transfers the PCR plate to the Abbott m2000rt module for nucleic acid detection.

SUMMARY

Aspects of the present disclosure include sample preparation cartridges including a frame the includes a plurality of wells integrated therewith, where the plurality of wells have a closed bottom and an open top. The frame further includes an opening within the frame having a reaction vessel (RV) or RV cap removably disposed therein, where the plurality of wells and the opening are linearly arranged relative to each other. Also provided are sample preparation cartridges that include a frame, two or more cartridge separation projections on a top side of the frame, and two or more cartridge separation projections on a bottom side of the frame. The cartridge separation projections separate the cartridge and a different cartridge when the cartridge and different cartridge are stacked. Methods of using the sample preparation cartridges, as well as nucleic acid sample preparation units that include the sample preparation cartridges, are also provided.

DETAILED DESCRIPTION

Figure 1:
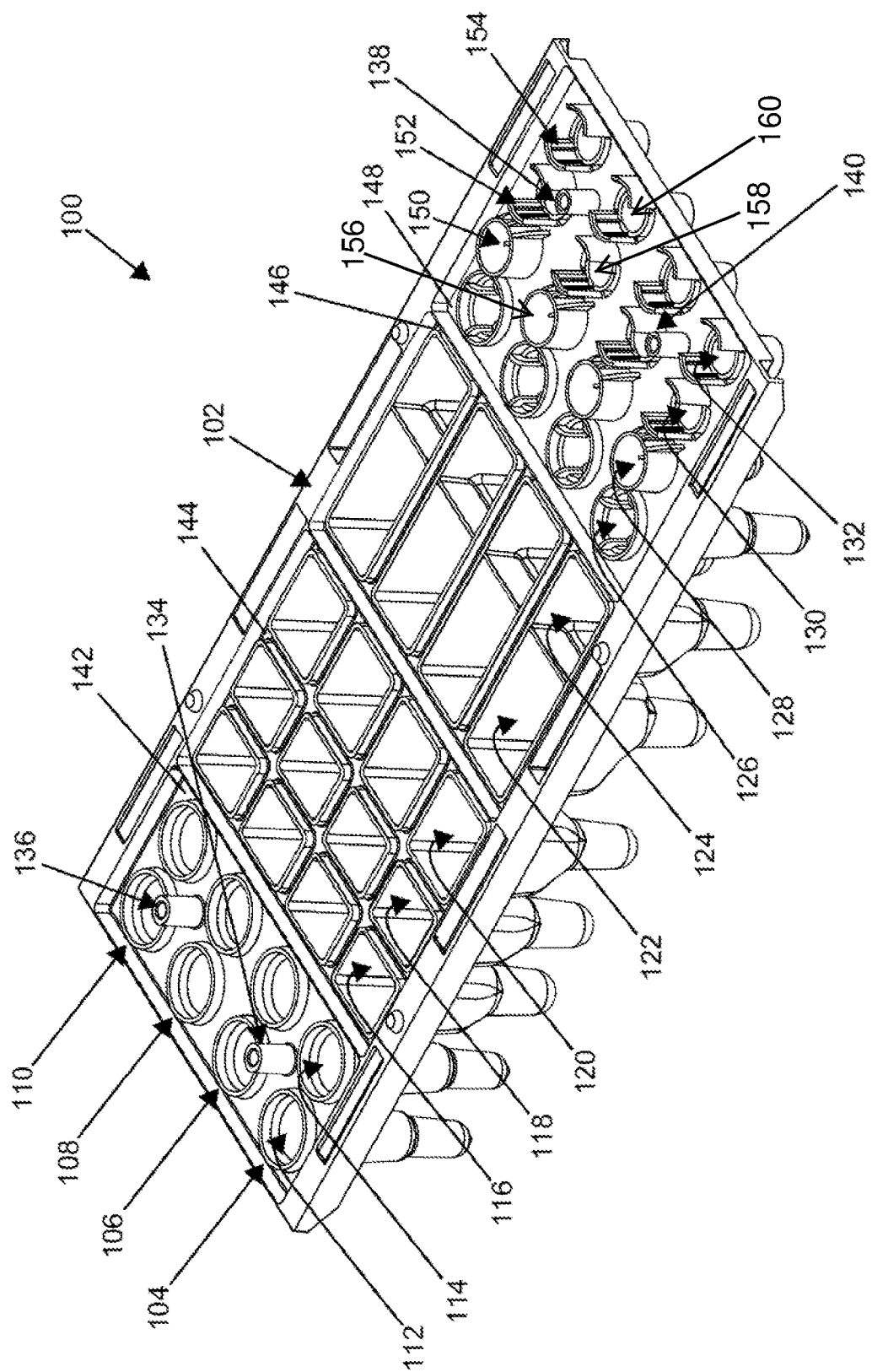
FIG. 1 shows a sample preparation cartridge according to one embodiment of the present disclosure. In this example, the cartridge includes first, second, third and fourth pluralities of linearly arranged wells. Each plurality of linearly arranged wells is also linearly arranged with openings in the frame of the cartridge.

Aspects of the present disclosure include sample preparation cartridges including a frame the includes a plurality of wells integrated therewith, where the plurality of wells have a closed bottom and an open top. The frame further includes an opening within the frame having a reaction vessel (RV) or RV cap removably disposed therein, where the plurality of wells and the opening are linearly arranged relative to each other. Also provided are sample preparation cartridges that include a frame, two or more cartridge separation projections on a top side of the frame, and two or more cartridge separation projections on a bottom side of the frame. The cartridge separation projections separate the cartridge and a different cartridge when the cartridge and different cartridge are stacked. Methods of using the sample preparation cartridges, as well as nucleic acid sample preparation units that include the sample preparation cartridges, are also provided.

Before the present sample preparation cartridges, methods, and sample preparation units are described in greater detail, it is to be understood that the present disclosure is not limited to particular embodiments described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the present sample preparation cartridges, methods, and sample preparation units. The upper and lower limits of these smaller ranges may independently be included in the smaller ranges and are also encompassed within the sample preparation cartridges, methods, and sample preparation units, subject to any specifically excluded limit in the stated range. Where the stated range includes one or both of the limits, ranges excluding either or both of those included limits are also included in the sample preparation cartridges, methods, and sample preparation units.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present sample preparation cartridges, methods, and sample preparation units, representative illustrative sample preparation cartridges, methods, and sample preparation units are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present sample preparation cartridges, methods, and sample preparation units. Any recited method can be carried out in the order of events recited or in any other order which is logically possible.

Sample Preparation Cartridges

As summarized above, aspects of the present disclosure include sample preparation cartridges. According to certain embodiments, the sample preparation cartridges include a frame including a plurality of wells integrated therewith, where the plurality of wells have a closed bottom and an open top. The frame further includes an opening within the frame having a reaction vessel (RV) or RV cap removably disposed therein. The plurality of wells and the opening are linearly arranged relative to each other.

In certain aspects, a RV is removably disposed in the opening, e.g., an opening that is open at the bottom, or an opening that is closed at the bottom. When a RV is removably disposed in the opening, the opening may be a first opening, and the frame may include a second opening in which a RV cap is removably disposed. The second opening may be open at the bottom or closed at the bottom.

According to certain embodiments, the plurality of wells is a first plurality of wells, and the frame includes a second plurality of linearly arranged wells integrated therewith, where the second plurality of wells have a closed bottom and an open top. In these embodiments, the frame includes an opening within the frame linearly arranged with the second plurality of wells. The opening linearly arranged with the second plurality of wells has a RV or RV cap removably disposed therein.

In certain aspects, when the cartridge includes first and second pluralities of linearly arranged wells as described above, the frame further includes a third plurality of linearly arranged wells integrated therewith, where the third plurality of wells have a closed bottom and an open top. According to this embodiment, the frame includes an opening within the frame linearly arranged with the third plurality of wells. The opening linearly arranged with the third plurality of wells has a RV or RV cap removably disposed therein.

According to certain embodiments, when the cartridge includes first, second and third pluralities of linearly arranged wells as described above, the frame further includes a fourth plurality of linearly arranged wells integrated therewith, where the fourth plurality of wells have a closed bottom and an open top. According to this embodiment, the frame includes an opening within the frame linearly arranged with the fourth plurality of wells. The opening linearly arranged with the fourth plurality of wells has a RV or RV cap removably disposed therein.

The RV and/or RV cap present in the cartridges of the present disclosure may be any of the RVs or RV caps described, which claims priority to U.S. Ser. No. 62/308,620, the disclosures of which are incorporated herein by reference in their entireties.

The cartridges of the present disclosure may include a plunger removably disposed in an opening not occupied by a RV or RV cap. The plunger can be an elongate cover having a bore into which a magnetic rod may be inserted. A plunger finds use, e.g., for mixing fluids present in the wells of the cartridge, providing a surface onto which magnetic particles may be captured when a magnetic rod is inserted into the bore of the plunger. Upon capturing of the magnetic particles, the magnetic particles may be moved successively through wells of the cartridge for washing, etc. of nucleic acids present on the magnetic particles. The plunger may have a shape that nearly fills the volume of the bottom portion of one or more of the wells. This forces fluid in the wells to be driven up and down with a range large enough to adequately mix reagents therein (e.g., to wash, elute, etc. nucleic acids present on magnetic particles). The tip of the plunger may be fluted in order to provide enough space to ensure the fluid can easily flow up when the plunger is submerged in the liquid during the mixing.

A plunger of the instant disclosure may include an elongated hollow cone structure (240, FIG. 3A) and a top opening. The plunger may include a plurality of flutes (242, FIG. 3A) at the closed end. The distance that the flutes extend to the closed end of the plunger may vary but, in certain embodiments extend into a rounded tip but not to an end nub. The flute, being a groove in the plunger, defines a cavity (244, FIG. 3A) which may, in some instances, be collectively defined for all flutes of the plurality as defining an empty volume of space. The volume of space ascribed to the flutes may be determined from the difference in volume of the plunger with and without the flutes (that is, the difference between a plunger with the flutes and an identical plunger without the flutes). Such volume may or may not correspond to the volume of buffer used in one or more of the processing methods as describe herein.

Plungers of the instant disclosure may be configured to minimize contact of the plunger with the elution well. For example, in some instances, contact of a feature of the plunger with a well (e.g., an elution well) may generally prevent further contact of surfaces of plunger with the well. In some instances, contact of a nub feature of the plunger with the elution well may prevent further contact of surfaces of the plunger with the elution well. In some instances, contact of one or more flute features of the plunger with the well may prevent further contact of surfaces of the plunger with the well. In some instances, the general shape of the plunger, in relationship to the shape of the well, is configured to minimize contact between surfaces of the plunger with surfaces of the well, including but not limited to e.g., one or more tapers of the plunger, the contours of end of the plunger (e.g., contours of the rounded end of the plunger), etc. For example, in some instances, the plunger end and the bottom of an elution well are of sufficiently dissimilar shape so as to minimize contact of surfaces of the plunger with surfaces of the elution well. Plungers that find use in the SP cartridges, methods and sample preparation units of the present disclosure include those described, e.g., which claims priority to U.S. Ser. No. 62/308,645, the disclosures of which are incorporated herein by reference in their entireties.

Figure 3:
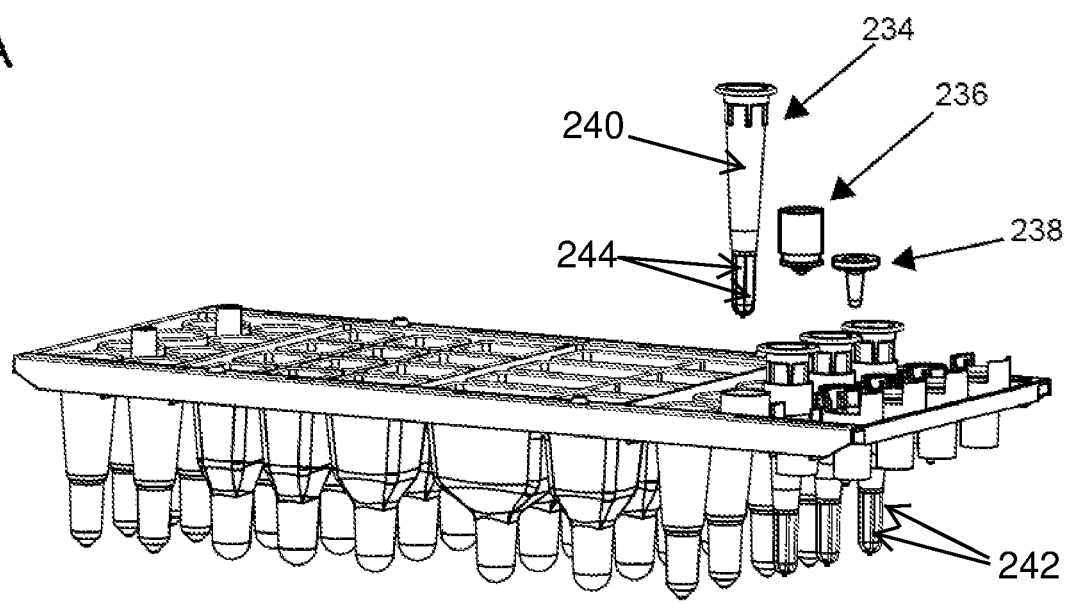
FIG. 3, Panels A and B, show a sample preparation cartridge according to one embodiment of the present disclosure. Panel A shows a cartridge similar to that shown in FIG. 2, with the plunger, RV cap and RV shown above their respective openings. Panel B is a side view of a sample preparation cartridge according to one embodiment.
Figure 3:
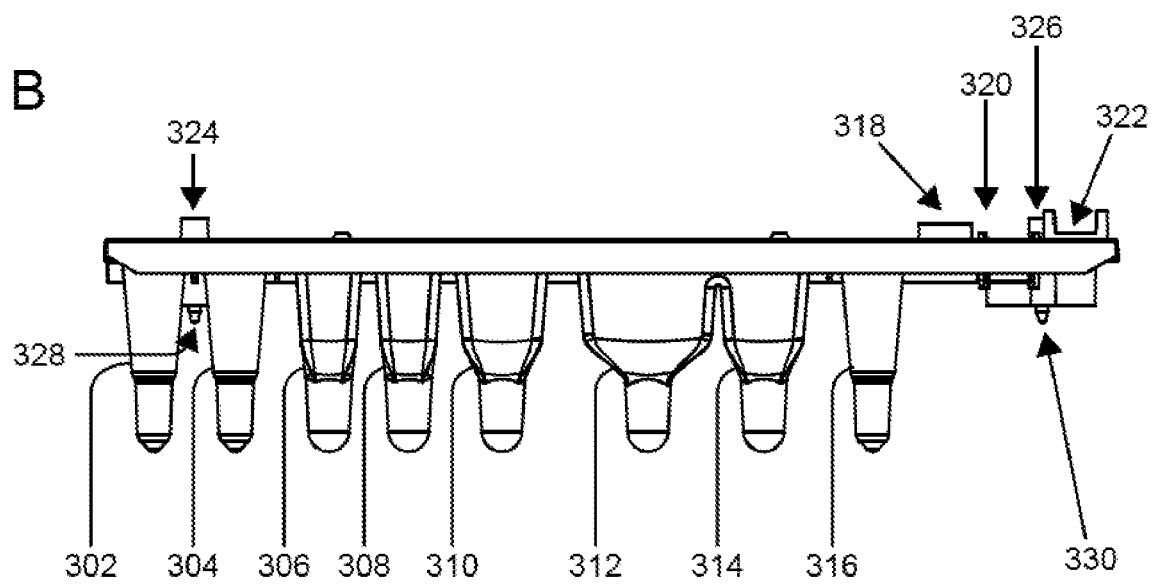

The opening in which the plunger is removably disposed may be open or closed at the bottom. In certain aspects, an opening that is open at the bottom finds use in holding an unused plunger. In certain aspects, an opening that is closed at the bottom finds use in holding a used plunger, e.g., to contain any residual liquid sample preparation reagents present on the plunger upon completion of preparing a sample. An example of a plunger according to one embodiment is shown in FIG. 3, Panel A.

Sample preparation cartridges of the present disclosure may include two or more cartridge separation projections on a top side of the frame and two or more cartridge separation projections on a bottom side of the frame, where the cartridge separation projections separate the cartridge and a different cartridge when the cartridge and different cartridge are stacked. In certain aspects, a cartridge includes four cartridge separation projections on the top side of the frame and four cartridge separation projections on the bottom side of the frame. The top and bottom projections may be configured (e.g., have a length, diameter, taper, and or the like) to provide a desired level of separation between the frames of stacked cartridges. Such separation finds use, e.g., when plungers are present in openings of the stacked cartridges, e.g., to reduce or eliminate the possibility of the plungers becoming dislodged upon stacking and/or unstacking of the cartridges.

The number of wells in a plurality of linearly arranged wells may vary. In certain aspects, a cartridge of the present disclosure has 2 or more, 3 or more, 4 or more, 5 or more, 6 or more, 7 or more, 8 or more, 9 or more, or 10 or more wells. According to certain embodiments, a cartridge of the present disclosure has 20 or fewer, 15 or fewer, or 10 or fewer (e.g., 8 or fewer) numbers of wells. A cartridge may include from 2 to 10 wells, e.g., from 4 to 8 wells.

In certain aspects, the cartridges of the present disclosure are disposable. A disposable cartridge may be made of any suitable material, including a plastic material such as polystyrene, polypropylene, and the like.

A sample preparation cartridge according to one embodiment of the present disclosure is shown in FIG. 1. In this example, cartridge 100 includes frame 102, first plurality of linearly arranged wells 104, second plurality of linearly arranged wells 106, third plurality of linearly arranged wells 108, and fourth plurality of linearly arranged wells 110. The wells of the first, second, third and fourth plurality of wells are identical in this example, and for first plurality 104 include well 112, well 114, well 116, well 118, well 120, well 122, well 124, and well 126.

In this example, frame 102 further includes—for each of the first, second, third and fourth plurality of wells—three openings linearly arranged with their respective plurality of linearly arranged wells. First plurality of linearly arranged wells 104, for example, includes openings 128, 130 and 132. Similarly, the third plurality of linearly arranged wells 108, for example, includes openings 156, 158, and 160 as shown in FIG. 1.

Also included in this example are cartridge separation projections 134, 136, 138 and 140 on the top side of the frame, and four corresponding cartridge separation projections on the bottom side of the frame (not shown). The cartridge separation projections on the top side of the frame have openings into which corresponding cartridge separation projections on the bottom side of the frame of a different cartridge can mate, to provide a desired degree of separation between the two cartridges when the different cartridge is stacked on top of cartridge 100. Such separation finds use, e.g., when plungers are present in openings of the stacked cartridges, e.g., to reduce or eliminate the possibility of the plungers becoming dislodged upon stacking and/or unstacking of the cartridges.

In this example, frame 102 includes trenches 142, 144, 146 and 148 surrounding their respective groups of wells. The trenches find use, e.g., in containing any overflow of liquid sample preparation reagents during filling of the wells and/or the sample preparation process.

Figure 2:
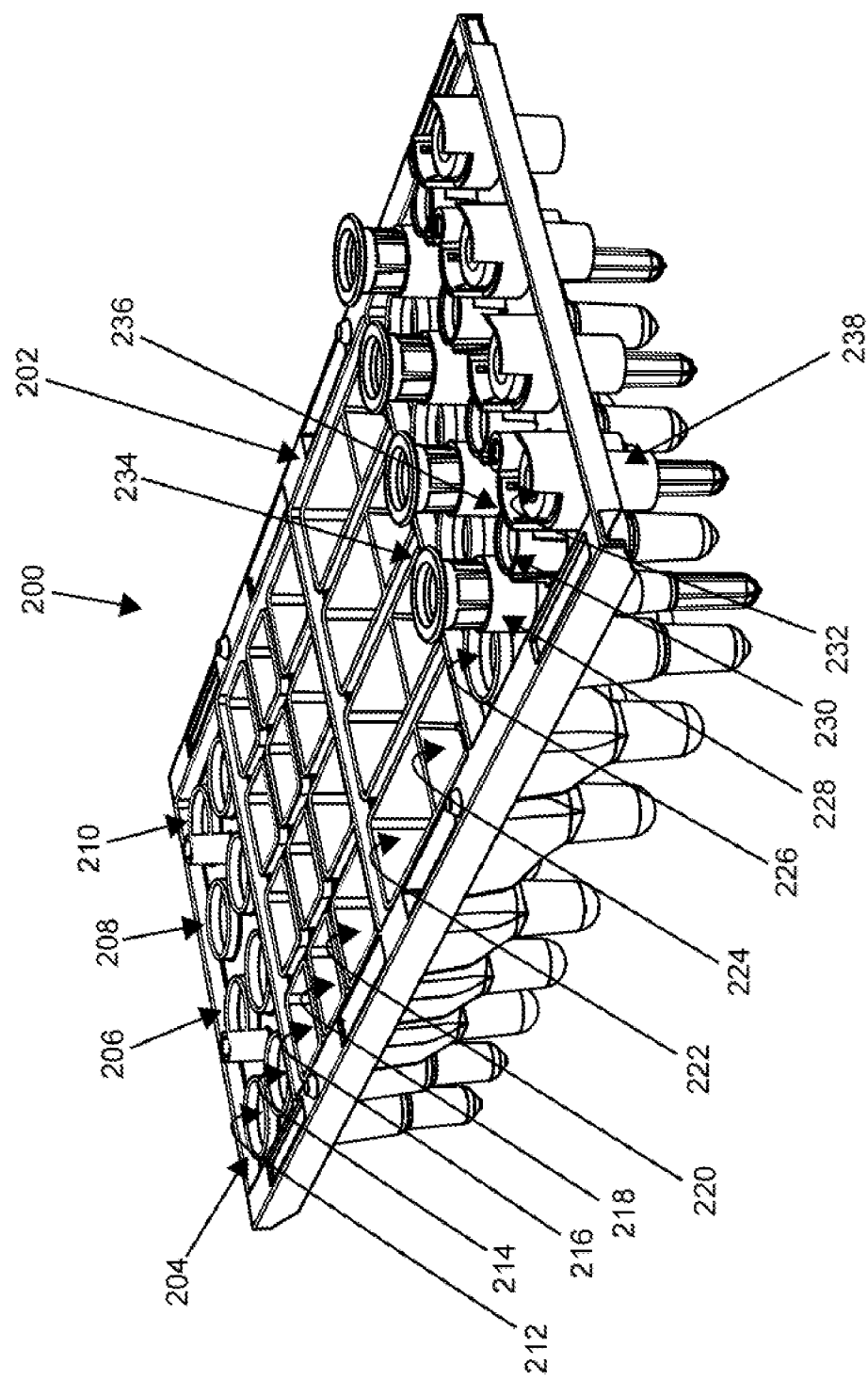
FIG. 2 shows a sample preparation cartridge according to one embodiment of the present disclosure. In this example, the cartridge includes first, second, third and fourth pluralities of linearly arranged wells. Each plurality of linearly arranged wells is also linearly arranged with openings in the frame of the cartridge, the openings having removably disposed therein a reaction vessel (RV), a RV cap, and a plunger.

FIG. 2 shows a sample preparation cartridge according to one embodiment. Here, cartridge 200 includes frame 202, first plurality of linearly arranged wells 204, second plurality of linearly arranged wells 206, third plurality of linearly arranged wells 208, and fourth plurality of linearly arranged wells 210. The wells of the first, second, third and fourth plurality of wells are identical in this example, and for first plurality 204 include well 212, well 214, well 216, well 218, well 220, well 222, well 224, and well 226. In this example, frame 202 further includes—for each of the first, second, third and fourth plurality of wells—three openings linearly arranged with their respective plurality of linearly arranged wells. First plurality of linearly arranged wells 204, for example, includes openings 228, 230 and 232. Shown in FIG. 2 are plunger 234, RV cap 236 and RV 238, each removably disposed in openings 228, 230 and 232, respectively. Also included in this example are cartridge separation projections and trenches similar to those described above with respect to FIG. 1.

FIG. 3, Panel A shows a cartridge similar to that shown in FIG. 2, with the plunger 234, RV cap 236 and RV 238 shown above their respective openings. FIG. 3, Panel B is a side view of the cartridge shown in Panel A, showing a first plurality of linearly arranged wells that includes wells 302, 304, 306, 308, 310, 312, 314 and 316. As with any of the wells of any of the cartridges described herein, the wells find use, e.g., in containing sample preparation reagents independently selected from: elution buffer, molecular grade water, nucleic acid wash solution, lysis buffer, pretreatment solution (e.g., for protease incubation with sample), vapor barrier liquid (e.g., an oil) for overlaying on a PCR reaction mixture present in the RV to prevent evaporation during, e.g., thermocycling. According to one embodiment, wells 302, 304, 306, 308, 310, 312, 314 and 316 find use, respectively, for containing: elution buffer; molecular grade water; nucleic acid wash solution; nucleic acid wash solution; nucleic acid wash solution; lysis buffer; pretreatment reagent; and a used plunger (and optionally, vapor barrier liquid). Shown in Panel B are openings 318, 320 and 322 linearly arranged with their respective plurality of linearly arranged wells, the openings finding use, e.g., for holding a plunger, RV cap, and RV, respectively.

Also shown in FIG. 3, Panel B are top cartridge separation projections 324 and 326, and bottom cartridge separation projections 328 and 330. When two such cartridges are stacked, bottom projections 328 and 330 will mate with (insert into) top projections of a different cartridge corresponding to top projections 324 and 326. The top and bottom projections may be configured (e.g., have a length, diameter, taper, and or the like) to provide a desired level of separation between the frames of stacked cartridges.

In certain aspects, one or more of the openings for holding a plunger, RV cap, RV, and/or the like may include a structural feature that secures and/or aligns the plunger, RV cap, RV, and/or the like in its respective opening, while still rendering the plunger, RV cap, RV, and/or the like removable by a plunger bar, pipettor, and/or the like. For example, the one or more openings may include a feature that protrudes, e.g., radially, into the opening such that upon disposing the plunger, RV cap, RV, and/or the like into its respective opening, the plunger, RV cap, RV, and/or the like is securely disposed and/or aligned in the opening during movement, jostling, etc. of the sample preparation cartridge. In some embodiments, one or more of the openings for holding a plunger, RV cap, RV, and/or the like may include one or more crush ribs (150, 152, and 154 of FIG. 1) for securely disposing and/or aligning the plunger, RV cap, RV, and/or the like in its respective opening. The crush ribs may have any suitable design. In certain aspects, the crush ribs are pointed. That is, the portion of the rib(s) that contact the plunger, RV cap, RV, and/or the like upon disposing the plunger, RV cap, RV, and/or the like into the opening is pointed. In other aspects, the portion of the rib(s) that contact the plunger, RV cap, RV, and/or the like upon disposing the plunger, RV cap, RV, and/or the like into the opening is rounded.

Methods

As summarized above, provided by the present disclosure are methods. In certain aspects, the methods are methods of preparing a nucleic acid sample. Such methods include lysing a cellular sample in a lysis well of a sample preparation cartridge (e.g., any of the cartridges described above) to produce a lysed sample, and washing nucleic acids present in the lysed sample, where the washing includes transferring nucleic acids from the lysed sample in the lysis well successively to two or more wash wells of the cartridge. The methods further include transferring the washed nucleic acids from a final wash well of the two or more wash wells to an elution well of the cartridge. The methods further include eluting the nucleic acids and transferring the eluted nucleic acids to a reaction vessel (RV) removably disposed in an opening of the cartridge.

In certain aspects, the cellular sample is a collection cells, e.g., from whole blood, serum, plasma, a tissue, organ, and/or the like of a mammal (e.g., a human, a rodent (e.g., a mouse), or any other mammal of interest). In other aspects, the cellular sample is a collection cells from a source other than a mammal, such as bacteria, yeast, insects (e.g., drosophila), amphibians (e.g., frogs (e.g., Xenopus)), viruses, plants, or any other non-mammalian nucleic acid sample source.

According to certain embodiments, transferring the nucleic acids from the lysis well to the two or more wash wells includes capturing the nucleic acids on magnetic particles present in the lysis well and transferring the magnetic particles having the nucleic acids captured thereon successively to the two or more wash wells.

In certain aspects, transferring the nucleic acids from the final wash well of the two or more wash wells to the elution well includes capturing the nucleic acids on magnetic particles in the final wash well and transferring the magnetic particles having the nucleic acids captured thereon to the elution well.

The manner in which the eluted nucleic acids are transferred to the RV removably disposed in the opening of the cartridge may vary. For example, transferring the eluted nucleic acids to the RV may include aspirating the eluted nucleic acids from the elution well and directly dispensing the eluted nucleic acids into the RV.

In other aspects, transferring the eluted nucleic acids to the RV includes: aspirating the eluted nucleic acids from the elution well and dispensing the eluted nucleic acids into a well that includes assay reagents to form a reaction mixture, where the well that includes assay reagents is not a well of the cartridge; and aspirating the reaction mixture from the well that includes the assay reagents and dispensing the reaction mixture into the RV, either directly or successively through one or more additional reagent wells. According to certain embodiments, dispensing the eluted nucleic acids into a well that includes assay reagents includes dispensing the eluted nucleic acids into a well that includes lyophilized assay reagents. Any of the aspirating and dispensing steps described herein may be performed using a pipettor, e.g., a robotic pipettor, such as a robotic pipettor of an automated sample preparation system.

Assay reagent of interest include, but are not limited to, polymerase chain reaction (PCR) reagents, including reagents suitable for real-time nucleic acid amplification and detection. In certain aspects, the reagents are suitable for amplification and/or detection of a nucleic acid target from one or more of human immunodeficiency virus (HIV), Hepatitis C virus (HCV), Hepatitis B virus (HBV), Chlamydia trachomatis (CT), Neisseria gonorrhoeae (NG), Human papillomavirus (HPV), Cytomegalovirus (CMV), Epstein-Barr virus (EBV), Polyomavirus BK (BKV), Methicillin-resistant *Staphylococcus aureus* (MRSA), *Clostridium difficile* (C. Diff.), Vancomycin-resistant enterococci (VRE), adenovirus, *Mycobacterium tuberculosis* (TB), Varicella Zoster Virus (VZV), Herpes simplex virus (HSV), John Cunningham virus (JCV), enterovirus, Lymphogranuloma Venereum (LGV), viruses of a Respiratory Viral Panel (RVP), Human Herpesvirus 6 (HHV6), *Trichomonas vaginalis, Mycoplasma genitalium*, norovirus, and zika virus.

The methods of the present disclosure may include additional steps, including, e.g., capping the RV with an RV cap. In certain aspects, the capping is performed using a pipettor. For example, the capping may include picking up an RV cap removably disposed in an opening of the cartridge and inserting a bottom portion of the RV cap into an upper opening of the RV, where the picking up and inserting are performed using a pipettor, e.g., a robotic pipettor. In certain aspects, picking up the cap includes friction fitting a barrel of a pipettor to the RV cap by inserting a distal end of the barrel into a complementary indentation in the top of the RV cap. The friction fit allows the RV cap to be picked up by the pipettor, transferred by the pipettor to the RV, and inserted into the complementary indentation in the top of the RV cap, thereby sealing the RV with the RV cap. The pipettor may include a release mechanism to release the RV cap, e.g., using one or more extensions on the barrel that extend away from the barrel while in contact with the RV cap, to separate the barrel from the RV cap.

Figure 4:
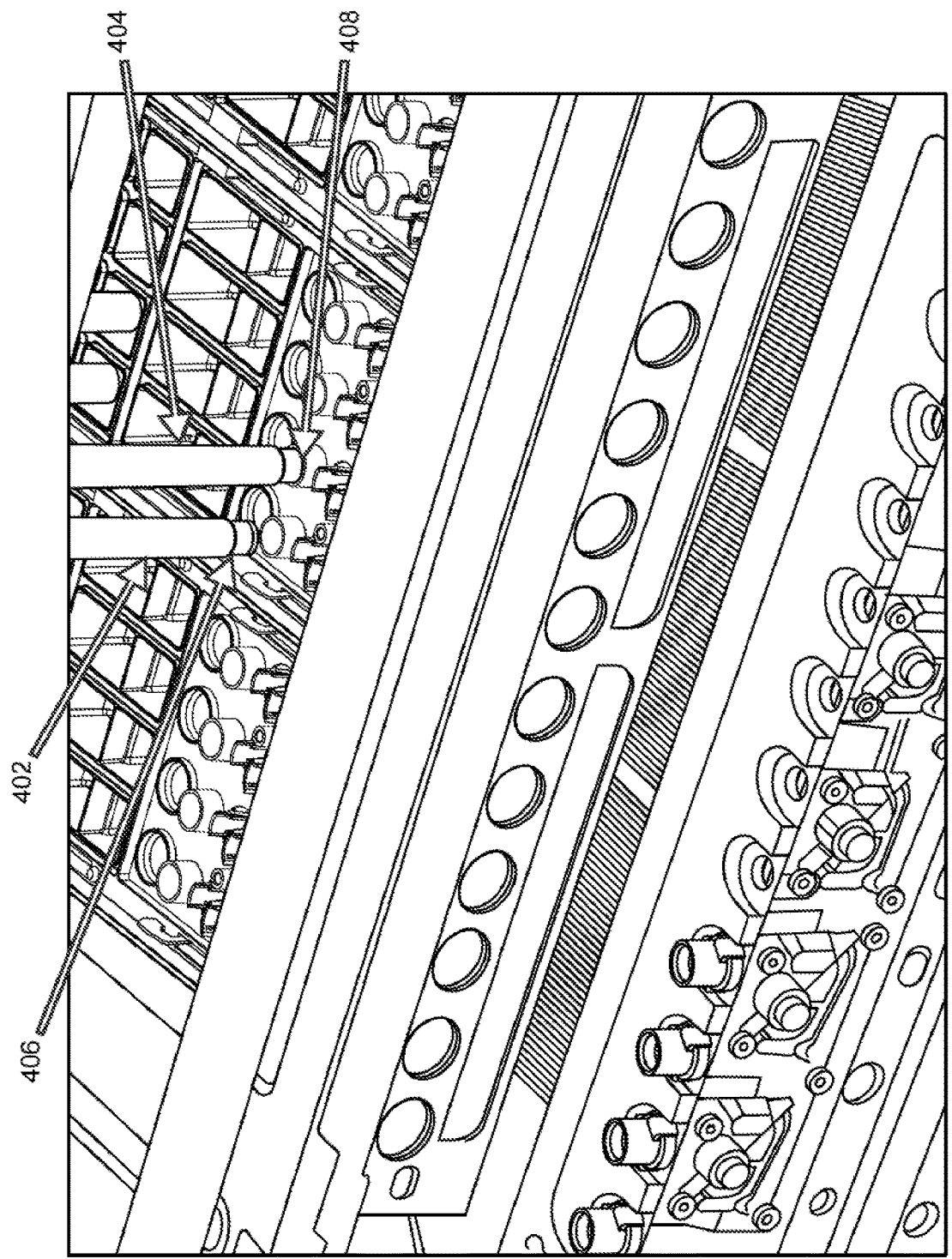
FIG. 4 shows the picking up of reaction vessel (RV) caps by a robotic pipettor according to one embodiment.

FIG. 4 shows an illustration of a robotic pipettor picking up reaction vessel (RV) caps present in a sample preparation cartridge at a sample preparation unit. Shown are pipettor barrels 402 and 404 of a robotic pipettor attached to RV caps 406 and 408 in preparation for capping RVs present at adjacent positions of the sample preparation cartridge.

Figure 5:
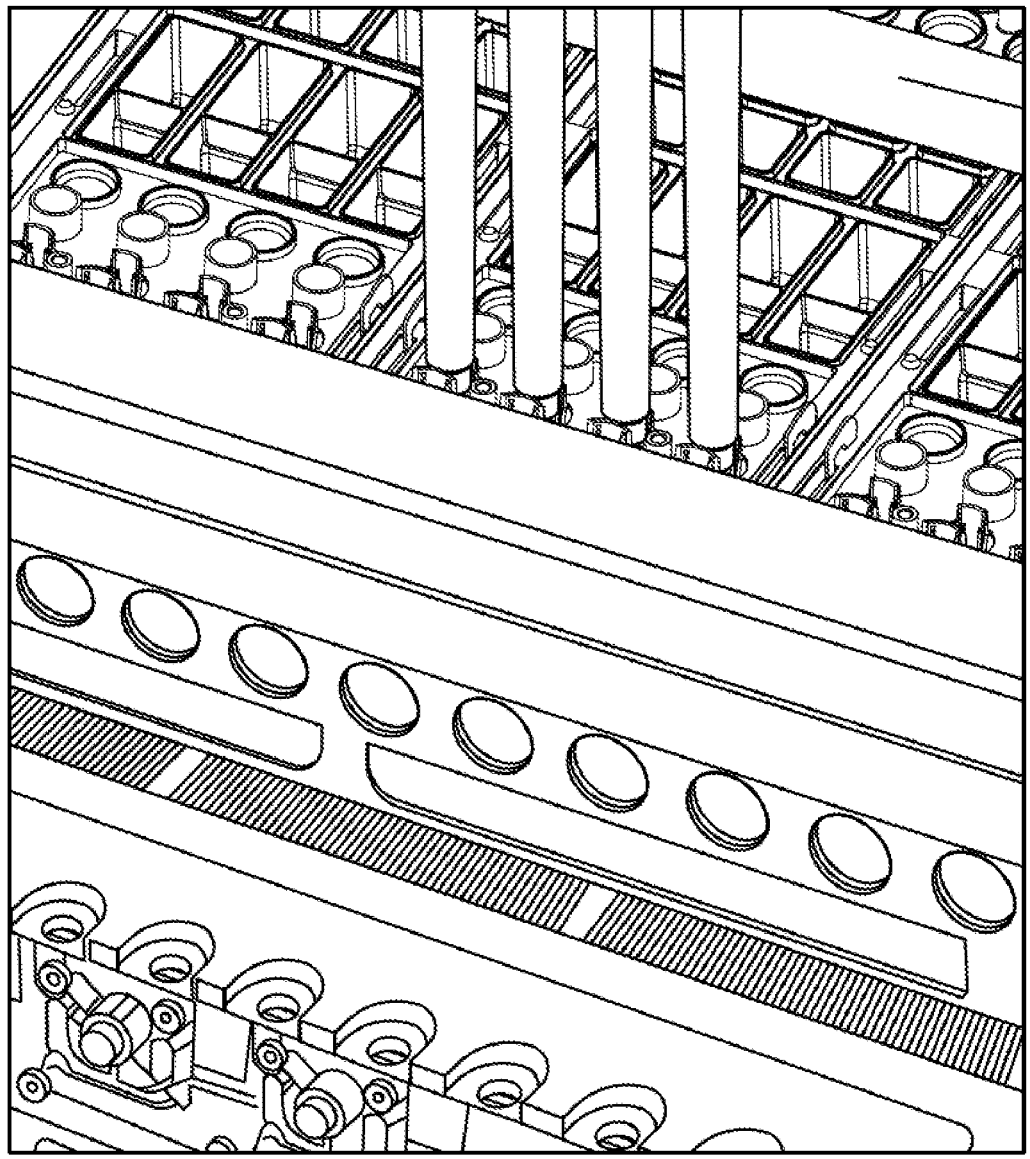
FIG. 5 shows the capping of RVs by a robotic pipettor according to one embodiment.

An illustration showing the capping of RVs with RV caps by a robotic pipettor according to one embodiment is provided in FIG. 5. In this example, the pipettor has four barrels, each of which is pushing an RV cap into a respective RV in a sample preparation cartridge at a sample preparation unit.

Figure 6:
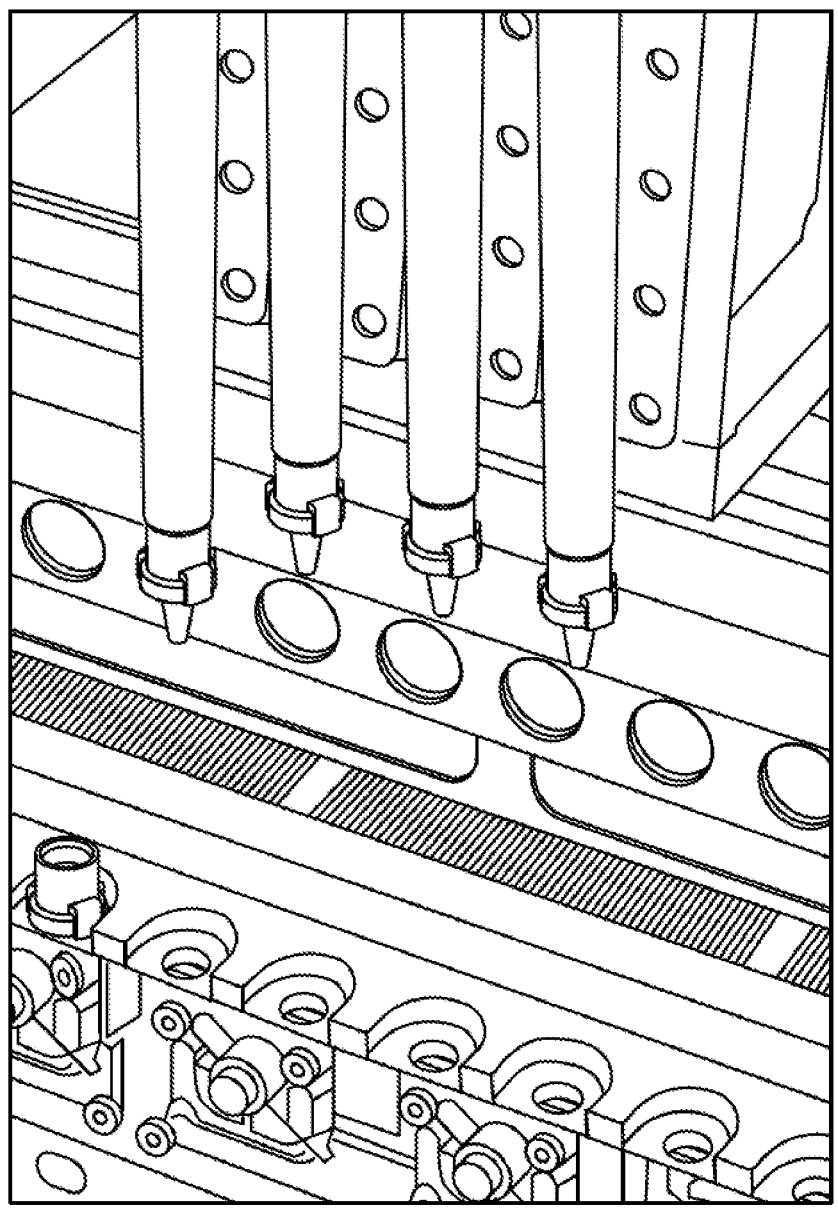
FIG. 6 shows the transfer of capped RVs from an SP cartridge to wells of a sample analysis unit according to one embodiment.

FIG. 6 shows the transport of capped RVs from a sample preparation cartridge to RV wells of a sample analysis unit by a robotic pipettor. The distal ends of the 4 pipettor barrels are mated with the RV caps of the capped RVs, enabling the transport of the capped RVs by the robotic pipettor.

Sample Preparation Units

Also provided by the present disclosure are sample preparation units. In certain aspects, the sample preparation units are nucleic acid sample preparation units. According to certain embodiments, a nucleic acid sample preparation unit (SPU) includes one or more (e.g., two or more) sample preparation cartridges (e.g., any of the cartridges described herein), and a magnetic particle transfer component. In some instances, a SPU of the present disclosure is present in an automated nucleic acid sample preparation and analysis system. For example, the SPU may be present and employed in an automated system as described in e.g., which claims priority to U.S. Ser. No. 62/308,617 and U.S. Ser. No. 62/357,772, the disclosures of which are incorporated herein by reference in their entireties.

A magnetic particle transfer component may include a plunger magnet bar suspended above the one or more sample preparation cartridges, and a magnetic rod for each plurality of linearly arranged wells, the magnetic rod(s) attached to the plunger magnet bar and projecting from the plunger magnet bar toward the plurality of linearly arranged wells. The magnetic particle transfer component may further include a plunger bar suspended above the one or more sample preparation cartridges, the plunger bar including a plunger attachment point for each plurality of linearly arranged wells. The plunger bar is at a position lower than the plunger magnet bar, such that the magnetic rods are positioned above their corresponding plungers and capable of being inserted into and removed from bores of the plungers.

The magnetic particle transfer component further includes a horizontal translation drive for translating the plunger magnet bar (and accordingly, magnetic rods) and the plunger bar (and accordingly, plungers, when present) across the plurality of linearly arranged wells. The magnetic particle transfer component further includes a vertical plunger magnet bar and plunger bar translation drive for coupled vertical translation of the plunger magnet bar and the plunger bar, and a vertical magnetic rod translation drive for independent vertical translation of the plunger magnet bar (and accordingly, magnetic rods), for inserting and removing the magnetic rod into a plunger attached to the plunger bar at the plunger bar attachment point. According to certain embodiments, the plunger attachment point is a fork that couples with complementary grooves an upper portion of the plunger.

In some cases, the plunger bar may perform a movement prior to aligning with an element of the plunger to pick up the plunger, e.g., the plunger bar may perform a movement that repositions the plunger within the sample preparation cartridge. In one embodiment, the plunger bar may perform a motion such that a portion of the plunger bar or an element attached thereto (e.g., a grasping component, such as the above-described fork) is used to tap down the plunger, e.g., to seat the plunger in the sample processing cartridge. In some instances, seating the plunger in the sample processing cartridge assures that a grasping component properly aligns with a complementary feature of the plunger so that the plunger can be picked up by the plunger bar via grasping component.

A nucleic acid sample preparation unit of the present disclosure may include a heater disposed beneath the plurality of linearly arranged wells, where the heater is movable between a first position and a second position. The heater is in thermal communication with one or more of the linearly arranged wells in the first position (so as to heat the wells (and accordingly, reagents therein) when in the first position) and not in thermal communication with any of the linearly arranged wells in the second position.

Figure 7:
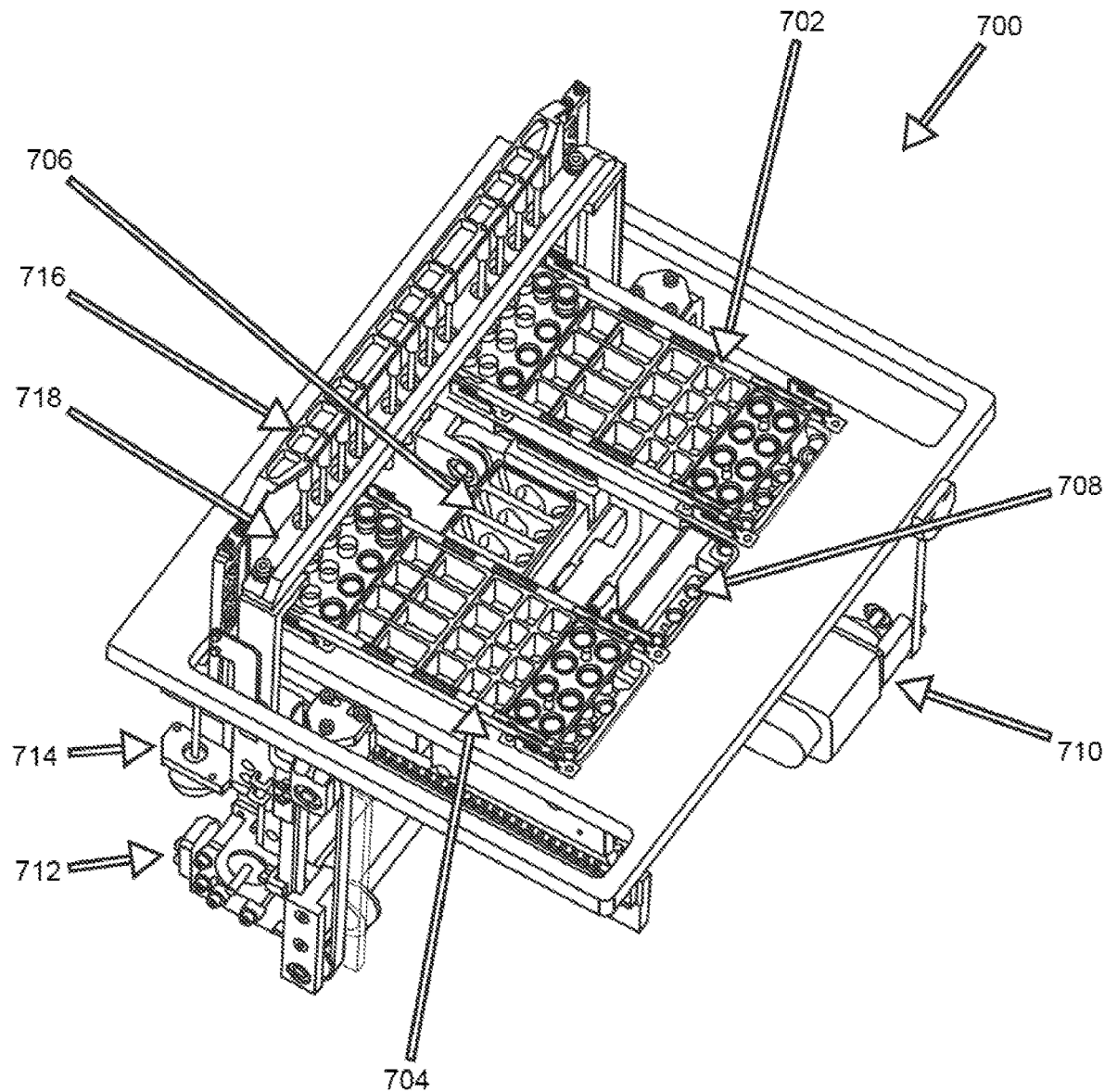
FIG. 7 shows a sample preparation unit according to one embodiment of the present disclosure.

A nucleic acid sample preparation unit (SPU) according to one embodiment is illustrated in FIG. 7. As shown, SPU 700 includes three sample preparation cartridge sample preparation positions, two of which are occupied in FIG. 7 by sample preparation cartridges 702 and 704. SPU 700 performs the mechanical motions needed to extract nucleic acid. SPU 700 has features to pull the mixing plunger from the cartridge and move it to different wells along the sample preparation cartridge to mix reagents. Mixing takes place using the plunger attached to a vertically translating plunger bar. The magnetic rods and plungers of SPU 700 are attached to plunger magnet bar 716 and plunger bar 718, respectively. SPU 700 also has two independently controllable and movable heaters. First heater 706 is used to heat reagents in pretreatment and lysis wells. Second heater 708 is used to heat fluid in an elution well. Both heaters can be engaged during mixing in their respective wells.

SPU 700 moves magnetic particles from one well to another by inserting a magnet into the plunger which attracts particles to the external wall of the plunger. Once the particles are magnetically attached to the plunger, they may be moved to the next well. The particles are released by removing the magnet from inside the plunger. Vertical motion of the plunger by SPU 700 causes mixing in the wells.

Simultaneous/coupled movement of the plungers and magnetic rods across the plurality of linearly arranged wells is enabled by a horizontal translation mechanism. In the embodiment shown in FIG. 7, the SPU includes Y-axis drive 710. Simultaneous/coupled vertical translation of the plungers and magnetic rods is effected by combination plunger bar and plunger magnet bar Z-axis drive 712. Independent vertical translation of the magnetic rods relative to the plungers is enabled by magnetic rod Z-axis drive 714. Drive 714 enables the insertion and removal of magnetic rods from their respective plungers during the sample preparation process.

Figure 8:
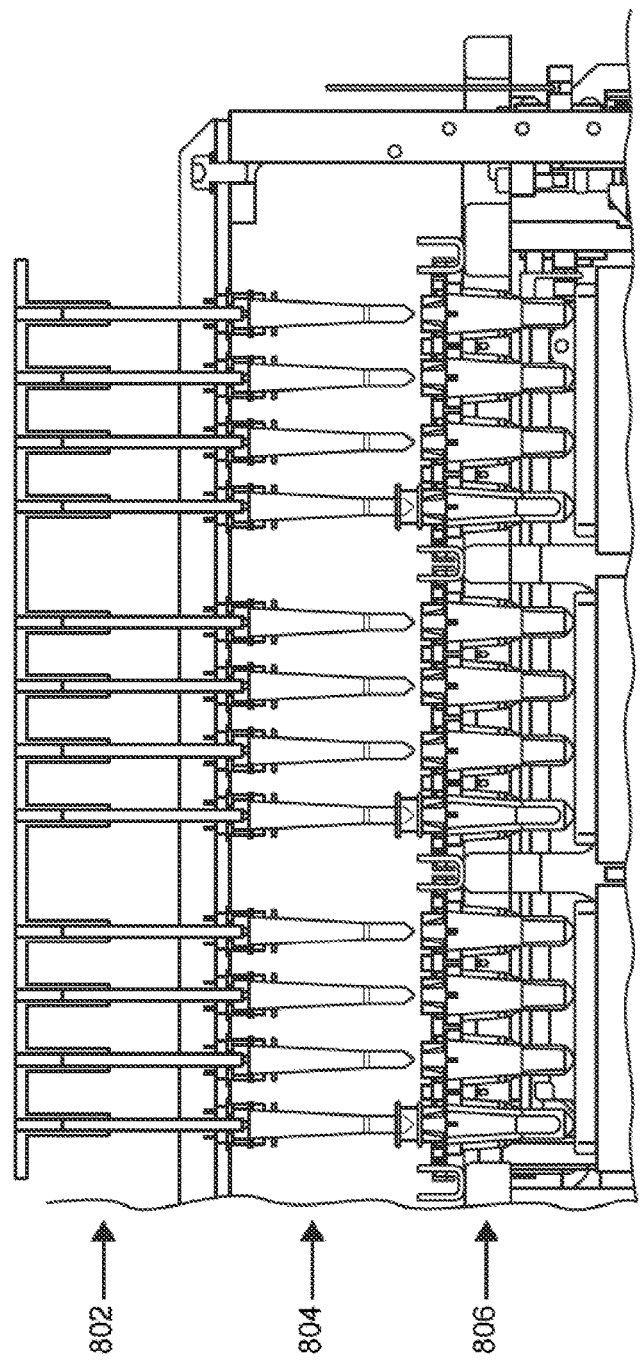
FIG. 8 shows magnetic rods, plungers, and cartridge wells of a sample preparation unit according to one embodiment of the present disclosure.
Figure 8:
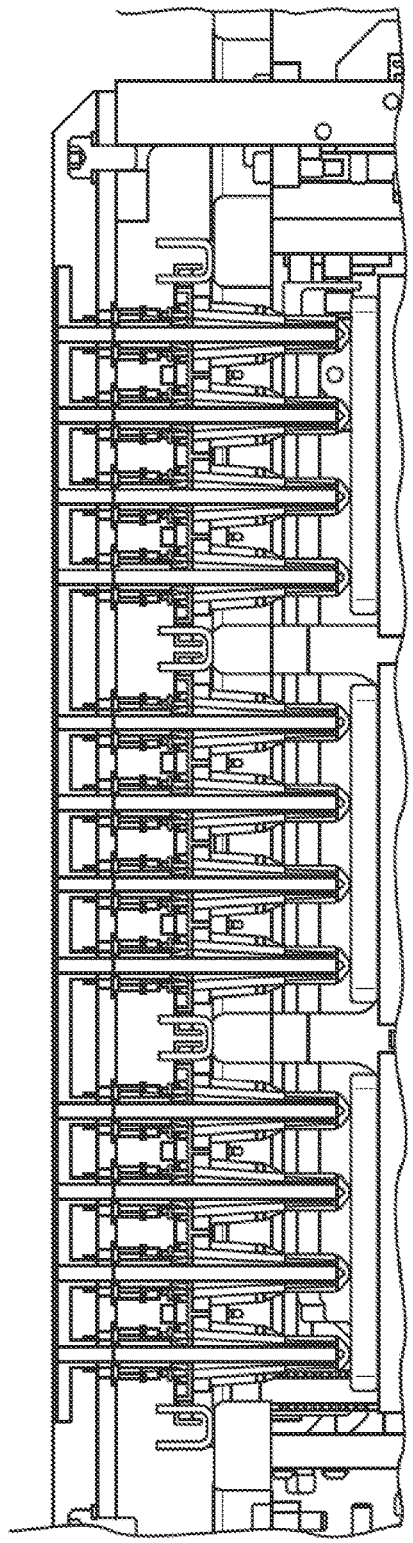

A side view of the SPU shown in FIG. 7 is illustrated in FIG. 8. Shown in the top panel of FIG. 8 are 3 groups of 4 magnets 802, 3 groups of 4 plungers 804, and 3 groups of 4 SP cartridge wells 806 of SP cartridges for holding plungers. Shown at the bottom of FIG. 8 are the elements in their down-most position, in which the magnets and plungers are collapsed in wells of the SP cartridges. This position is suitable for capturing magnetic particles present in the wells on a lower external wall of the plungers, enabling transfer of the particles to different wells, and release of the particles into the wells upon removal of the magnetic rod(s) from the plunger(s).

Another view of the SP module shown in FIG. 7 is illustrated at the bottom of FIG. 8. In this configuration, a magnetic rod is inserted into each plunger. Upon lowering into a well that includes magnetic particles having nucleic acids attached thereon, the magnetic particles will attach to the outside wall of the plunger, enabling movement of the particles from well to well for washing and, ultimately, elution of nucleic acids from the particles.

Notwithstanding the appended claims, the disclosure is also defined by the following clauses:

1. A sample preparation cartridge, comprising:
   a frame, comprising:
      a plurality of wells integrated therewith, wherein the plurality of wells have a closed bottom and an open top; and
      an opening within the frame having a reaction vessel (RV) or RV cap removably disposed therein,
      wherein the plurality of wells and the opening are linearly arranged relative to each other.
2. The sample preparation cartridge of Clause 1, wherein a RV is removably disposed in the opening.
3. The sample preparation cartridge of Clause 2, wherein the opening is open at the bottom.
4. The sample preparation cartridge of Clause 2, wherein the opening is closed at the bottom.
5. The sample preparation cartridge of any one of Clauses 2 to 4, wherein: the opening is a first opening, the frame comprises a second opening, and a RV cap is removably disposed in the second opening.
6. The sample preparation cartridge of Clause 1, wherein a RV cap is removably disposed in the opening.
7. The sample preparation cartridge of Clause 6, wherein the opening is open at the bottom.
8. The sample preparation cartridge of Clause 6, wherein the opening is closed at the bottom.
9. The sample preparation cartridge of any one of Clauses 6 to 8, wherein: the opening is a first opening, the frame comprises a second opening, and a RV is removably disposed in the second opening.
10. The sample preparation cartridge of any one of Clauses 1 to 9, wherein the plurality of wells is a first plurality of wells, and wherein the frame comprises:
    a second plurality of linearly arranged wells integrated therewith, wherein the second plurality of wells have a closed bottom and an open top; and
    an opening within the frame linearly arranged with the second plurality of wells, the opening linearly arranged with the second plurality of wells having a reaction vessel (RV) or RV cap removably disposed therein.
11. The sample preparation cartridge of Clause 10, comprising:
    a third plurality of linearly arranged wells integrated therewith, wherein the third plurality of wells have a closed bottom and an open top; and
    an opening within the frame linearly arranged with the third plurality of wells, the opening linearly arranged with the third plurality of wells having a reaction vessel (RV) or RV cap removably disposed therein.
12. The sample preparation cartridge of Clause 11, comprising:
    a fourth plurality of linearly arranged wells integrated therewith, wherein the fourth plurality of wells have a closed bottom and an open top; and
    an opening within the frame linearly arranged with the fourth plurality of wells, the opening linearly arranged with the fourth plurality of wells having a reaction vessel (RV) or RV cap removably disposed therein.
13. The sample preparation cartridge of any one of Clauses 1 to 12, comprising a plunger removably disposed in an opening not occupied by a RV or RV cap.
14. The sample preparation cartridge of Clause 13, wherein the opening in which the plunger is removably disposed is open at the bottom.
15. The sample preparation cartridge of Clause 14, wherein the plunger is an unused plunger.
16. The sample preparation cartridge of Clause 13, wherein the opening in which the plunger is removably disposed is closed at the bottom.
17. The sample preparation cartridge of Clause 16, wherein the plunger is a used plunger.
18. The sample preparation cartridge of any one of Clauses 1 to 17, comprising two or more cartridge separation projections on a top side of the frame and two or more cartridge separation projections on a bottom side of the frame, wherein the cartridge separation projections separate the cartridge and a different cartridge when the cartridge and different cartridge are stacked.
19. The sample preparation cartridge of Clause 18, comprising four cartridge separation projections on the top side of the frame and four cartridge separation projections on the bottom side of the frame.
20. The sample preparation cartridge of any one of Clauses 1 to 19, wherein the plurality of wells comprises from 2 to 10 wells.
21. The sample preparation cartridge of Clause 20, wherein the plurality of wells comprises from 4 to 8 wells.
22. A sample preparation cartridge, comprising:
    a frame comprising a plurality of linearly arranged wells integrated therewith, wherein the plurality of wells have a closed bottom and an open top; and
    two or more cartridge separation projections on a top side of the frame and two or more cartridge separation projections on a bottom side of the frame, wherein the cartridge separation projections separate the cartridge and a different cartridge when the cartridge and different cartridge are stacked.
23. The sample preparation cartridge of Clause 22, comprising four cartridge separation projections on the top side of the cartridge and four cartridge separation projections on the bottom side of the cartridge.
24. The sample preparation cartridge of Clause 22 or Clause 23, comprising an opening within the frame having a reaction vessel (RV) or RV cap removably disposed therein, wherein the plurality of wells and the opening are linearly arranged relative to each other.
25. The sample preparation cartridge of Clause 24, wherein a RV is removably disposed in the opening.
26. The sample preparation cartridge of Clause 24 or Clause 25, wherein the opening is open at the bottom.
27. The sample preparation cartridge of Clause 24 or Clause 25, wherein the opening is closed at the bottom.

28. The sample preparation cartridge of any one of Clauses 24 to Clause 27, wherein: the opening is a first opening, the frame comprises a second opening, and a RV cap is removably disposed in the second opening.
29. The sample preparation cartridge of any one of Clauses 22 to 28, wherein the plurality of wells is a first plurality of wells, and wherein the frame comprises:
    a second plurality of linearly arranged wells integrated therewith, wherein the second plurality of wells have a closed bottom and an open top; and
    an opening within the frame linearly arranged with the second plurality of wells, the opening linearly arranged with the second plurality of wells having a reaction vessel (RV) or RV cap removably disposed therein.
30. The sample preparation cartridge of Clause 29, comprising:
    a third plurality of linearly arranged wells integrated therewith, wherein the third plurality of wells have a closed bottom and an open top; and
    an opening within the frame linearly arranged with the third plurality of wells, the opening linearly arranged with the third plurality of wells having a reaction vessel (RV) or RV cap removably disposed therein.
31. The sample preparation cartridge of Clause 30, comprising:
    a fourth plurality of linearly arranged wells integrated therewith, wherein the fourth plurality of wells have a closed bottom and an open top; and
    an opening within the frame linearly arranged with the fourth plurality of wells, the opening linearly arranged with the fourth plurality of wells having a reaction vessel (RV) or RV cap removably disposed therein.
32. The sample preparation cartridge of any one of Clauses 22 to 31, comprising a plunger removably disposed in an opening not occupied by a RV or RV cap.
33. The sample preparation cartridge of Clause 32, wherein the opening in which the plunger is removably disposed is open at the bottom.
34. The sample preparation cartridge of Clause 33, wherein the plunger is an unused plunger.
35. The sample preparation cartridge of Clause 32, wherein the opening in which the plunger is removably disposed is closed at the bottom.
36. The sample preparation cartridge of Clause 35, wherein the plunger is a used plunger.
37. The sample preparation cartridge of any one of Clauses 22 to 36, wherein the plurality of wells comprises from 2 to 10 wells.
38. The sample preparation cartridge of Clause 37, wherein the integrated row of receptacles comprises from 4 to 8 wells.
39. A method of preparing a nucleic acid sample, comprising:
    lysing a cellular sample in a lysis well of the cartridge of any one of Clauses 1 to 21 to produce a lysed sample;
    washing nucleic acids present in the lysed sample, wherein the washing comprises transferring nucleic acids from the lysed sample in the lysis well successively to two or more wash wells of the cartridge;
    transferring the washed nucleic acids from a final wash well of the two or more wash wells to an elution well of the cartridge;
    eluting the nucleic acids; and
    transferring the eluted nucleic acids to a reaction vessel (RV) removably disposed in an opening of the cartridge.
40. The method according to Clause 39, wherein transferring the nucleic acids from the lysis well to the two or more wash wells comprises:
    capturing the nucleic acids on magnetic particles present in the lysis well; and
    transferring the magnetic particles having the nucleic acids captured thereon successively to the two or more wash wells.
41. The method according to Clause 39 or 40, wherein transferring the nucleic acids from the final wash well of the two or more wash wells to the elution well comprises:
    capturing the nucleic acids on magnetic particles in the final wash well; and
    transferring the magnetic particles having the nucleic acids captured thereon to the elution well.
42. The method according to any one of Clauses 39 to 41, wherein transferring the eluted nucleic acids to the RV removably disposed in an opening of the cartridge comprises aspirating the eluted nucleic acids from the elution well and dispensing the eluted nucleic acids into the RV.
43. The method according to any one of Clauses 39 to 41, wherein transferring the eluted nucleic acids to the RV removably disposed in an opening of the cartridge comprises:
    aspirating the eluted nucleic acids from the elution well and dispensing the eluted nucleic acids into a well comprising assay reagents to form a reaction mixture, wherein the well comprising assay reagents is not a well of the cartridge; and
    aspirating the reaction mixture from the well comprising assay reagents and dispensing the reaction mixture into the RV.
44. The method according to Clause 43, wherein dispensing the eluted nucleic acids into a well comprising assay reagents comprises dispensing the eluted nucleic acids into a well comprising lyophilized assay reagents.
45. The method according to any one of Clauses 39 to 44, comprising capping the RV with an RV cap using a pipettor.
46. The method according to Clause 45, wherein the capping comprises picking up an RV cap removably disposed in an opening of the cartridge and inserting a bottom portion of the RV cap into an upper opening of the RV, wherein the picking up and inserting are performed using the pipettor.
47. A nucleic acid sample preparation unit, comprising:
    one or more sample preparation cartridges according to any one of Clauses 1 to 21; and
    a magnetic particle transfer component comprising:
        a plunger magnet bar suspended above the one or more sample preparation cartridges;
        a magnetic rod for each plurality of linearly arranged wells, the magnetic rod attached to the plunger magnet bar and projecting from the plunger magnet bar toward the plurality of linearly arranged wells;
        a plunger bar suspended above the one or more sample preparation cartridges, the plunger bar comprising a plunger attachment point for each plurality of linearly arranged wells;
        a horizontal translation drive for translating the plunger magnet bar and the plunger bar across the plurality of linearly arranged wells;
        a vertical plunger magnet bar and plunger bar translation drive for coupled vertical translation of the plunger magnet bar and the plunger bar; and a vertical plunger magnet bar translation drive for inserting and removing the magnetic rod into a plunger attached to the plunger bar at the plunger attachment point.

48. The nucleic acid sample preparation unit of Clause 47, comprising a heater disposed beneath the plurality of linearly arranged wells, wherein the heater is movable between a first position and a second position, wherein the heater is in thermal communication with one or more of the linearly arranged wells in the first position and not in thermal communication with any of the linearly arranged wells in the second position.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A sample preparation cartridge, comprising:
    a frame comprising a first opening, a second opening and, a third opening, a plurality of wells integrated within the frame, wherein the plurality of wells has a closed bottom and an open top; and
    a reaction vessel (RV) removably disposed in the first opening, an RV cap removably disposed in the second opening, and a plunger removably disposed in the third opening within the frame, wherein the first, second, and third openings include a structural feature that secures and/or aligns the RV, RV cap, and the plunger in their respective openings,
and wherein the plurality of wells and the openings are arranged in a linear alignment relative to each other.

2. The sample preparation cartridge of claim 1, wherein one or more openings is/are open at the bottom of the frame.

3. The sample preparation cartridge of claim 1, wherein one or more openings is/are closed at the bottom of the frame.

4. The sample preparation cartridge of claim 1, wherein the plurality of wells is a first plurality of wells, and wherein the frame further comprises:
    a second plurality of linearly aligned wells integrated in a second opening within the frame, wherein the second plurality of wells have a closed bottom and an open top, and wherein the second plurality of wells is linearly aligned with the second opening; and
    a second reaction vessel (RV) or second RV cap is removably disposed in the second opening.

5. The sample preparation cartridge of claim 4, further comprising:
    a third plurality of linearly aligned wells integrated in a third opening within the frame, wherein the third plurality of wells have a closed bottom and an open top, and wherein the third plurality of wells is linearly aligned with the third opening; and
    a third reaction vessel (RV) or third RV cap is removably disposed in the third opening.

6. The sample preparation cartridge of claim 5, further comprising:
    a fourth plurality of linearly aligned wells integrated in a fourth opening within the frame, wherein the fourth plurality of wells have a closed bottom and an open top, and wherein the fourth plurality of wells is linearly aligned with the fourth opening; and
    a fourth reaction vessel (RV) or fourth RV is cap removably disposed in the fourth opening.

7. The sample preparation cartridge of claim 1, wherein the opening in which the plunger is removably disposed is closed at the bottom.

8. The sample preparation cartridge of claim 1, comprising two or more cartridge separation projections on a top side of the frame and two or more cartridge separation projections on a bottom side of the frame, wherein the cartridge separation projections separate the cartridge and a different cartridge when the cartridge and different cartridge are stacked.

9. The sample preparation cartridge of claim 8, comprising four cartridge separation projections on the top side of the frame and four cartridge separation projections on the bottom side of the frame.

10. The sample preparation cartridge of claim 1, wherein the plurality of wells comprises from 2 to 10 wells.

11. The sample preparation cartridge of claim 10, wherein the plurality of wells comprises from 4 to 8 wells.

12. A sample preparation cartridge, comprising:
    a frame comprising a first opening, a second opening and, a third opening and a plurality of linearly aligned wells integrated therewith, wherein the plurality of wells have a closed bottom and an open top;
    two or more cartridge separation projections on a top side of the frame and two or more cartridge separation projections on a bottom side of the frame, wherein the cartridge separation projections separate the cartridge and a different cartridge when the cartridge and different cartridge are stacked; and
    a reaction vessel (RV) removably disposed in the first opening, an RV cap removably disposed in the second opening, and a plunger removably disposed in the third opening within the frame, wherein the first, second, and third openings include a structural feature that secures and/or aligns the RV, RV cap, and the plunger in their respective openings, and wherein the plurality of wells and the openings are arranged in a linear alignment relative to each other.

13. The sample preparation cartridge of claim 12, comprising four cartridge separation projections on the top side of the cartridge and four cartridge separation projections on the bottom side of the cartridge.

14. The sample preparation cartridge of claim 12, wherein one or more openings is/are open at the bottom.

15. The sample preparation cartridge of claim 12, wherein one or more openings is/are closed at the bottom.

16. The sample preparation cartridge of claim 12, wherein the plurality of wells is a first plurality of wells, and wherein the frame further comprises:
    a second plurality of linearly aligned wells integrated in a second opening within the frame, wherein the second plurality of wells have a closed bottom and an open top, and wherein the second plurality of wells is linearly aligned with the second opening; and a second reaction vessel (RV) or second RV cap is removably disposed in the opening.

17. The sample preparation cartridge of claim 16, further comprising:
a third plurality of linearly aligned wells integrated in a third opening within the frame, wherein the third plurality of wells have a closed bottom and an open top, and wherein the third plurality of wells is linearly aligned with the third opening; and
a third reaction vessel (RV) or third RV cap removably disposed in the opening.

18. The sample preparation cartridge of claim 17, further comprising:
a fourth plurality of linearly aligned wells integrated in fourth opening within the frame, wherein the fourth plurality of wells have a closed bottom and an open top, and wherein the fourth plurality of wells is linearly aligned with the fourth opening; and
a fourth reaction vessel (RV) or fourth RV cap removably disposed in the opening.

19. The sample preparation cartridge of claim 12, wherein the opening in which the plunger is removably disposed is open at the bottom of the frame.

20. The sample preparation cartridge of claim 12, wherein the opening in which the plunger is removably disposed is closed at the bottom of the frame.

21. The sample preparation cartridge of claim 12, wherein the plurality of wells comprises from 2 to 10 wells.

22. The sample preparation cartridge of claim 21, wherein the plurality of wells comprises from 4 to 8 wells.

23. A nucleic acid sample preparation unit, comprising:
one or more sample preparation cartridges according to claim 1; and
a magnetic particle transfer component comprising:
a plunger magnet bar suspended above the one or more sample preparation cartridges;
a magnetic rod for each plurality of linearly arranged wells, the magnetic rod attached to the plunger magnet bar and projecting from the plunger magnet bar toward the plurality of linearly arranged wells;
a plunger bar suspended above the one or more sample preparation cartridges, the plunger bar comprising a plunger attachment point for each plurality of linearly arranged wells;
a horizontal translation drive for translating the plunger magnet bar and the plunger bar across the plurality of linearly arranged wells;
a vertical plunger magnet bar and plunger bar translation drive for coupled vertical translation of the plunger magnet bar and the plunger bar; and
a vertical plunger magnet bar translation drive for inserting and removing the magnetic rod into a plunger attached to the plunger bar at the plunger attachment point.

24. The nucleic acid sample preparation unit of claim 23, comprising a heater disposed beneath the plurality of linearly arranged wells, wherein the heater is movable between a first position and a second position, wherein the heater is in thermal communication with one or more of the linearly arranged wells in the first position and not in thermal communication with any of the linearly arranged wells in the second position.

25. The sample preparation cartridge of claim 1, wherein the structural feature that secures the RV or RV cap in their respective openings comprises crush ribs.

26. The sample preparation cartridge of claim 25, wherein the portion of the crush ribs that contact the RV or RV cap upon disposing the RV or RV cap into the opening is pointed or rounded.

27. The sample preparation cartridge of claim 1, wherein the plunger comprises a hollow cone structure and a top opening.

28. The sample preparation cartridge of claim 27, wherein the plunger comprises a plurality of flutes at a closed end of the plunger.

29. The sample preparation cartridge of claim 28, wherein the plurality of flute form grooves between the flutes.

30. The sample preparation cartridge of claim 1, wherein the structural feature that secures the RV, RV cap and/or the plunger in their respective openings comprises a protrusion into the opening such that upon disposing the plunger, RV cap, and/or RV into its respective opening, the plunger, RV cap, and RV is securely disposed and/or aligned in the opening.

* * * * *